United States Patent [19]

Inamori et al.

[11] Patent Number: 4,957,935
[45] Date of Patent: Sep. 18, 1990

[54] PHENYLTRIAZOLE DERIVATIVE AND INSECTICIDE

[75] Inventors: Masahito Inamori, Shizuoka; Tetsuo Horii, Fujieda; Tomonori Shimazu, Shizuoka; Masaji Sugaya, Shizuoka, all of Japan

[73] Assignees: Kumiai Chemical Industry Co., Ltd.; Ihara Chemical Industry Co., Ltd., both of Tokyo, Japan

[21] Appl. No.: 365,437

[22] Filed: Jun. 13, 1989

Related U.S. Application Data

[63] Continuation-in-part of Ser. No. 171,777, Mar. 22, 1988, Pat. No. 4,925,864.

[30] Foreign Application Priority Data

Mar. 27, 1987 [JP] Japan ................................. 62-73636
Nov. 11, 1987 [JP] Japan ................................ 62-284873

[51] Int. Cl.$^5$ ................. A01N 43/653; C07D 249/14
[52] U.S. Cl. ............................... 514/383; 514/422; 548/264.8; 548/265.6; 548/518
[58] Field of Search ............... 548/264.8, 265.6, 518; 514/383, 422

[56] References Cited

U.S. PATENT DOCUMENTS 4,097,599  6/1978  Evans et al. ................... 514/383
4,414,221  11/1983  Parsons et al. ................ 548/265.6

4,871,757  10/1989  Luthy et al. ................... 514/383

OTHER PUBLICATIONS

Tanaka et al., "Applications of Fluorinated, etc." CA 109:22902$_s$ (1988).

Primary Examiner—Glennon H. Hollrah
Assistant Examiner—Patricia L. Morris
Attorney, Agent, or Firm—Oblon, Spivak, McClelland, Maier & Neustadt

[57] ABSTRACT

A phenyltriazole compound having the formula:

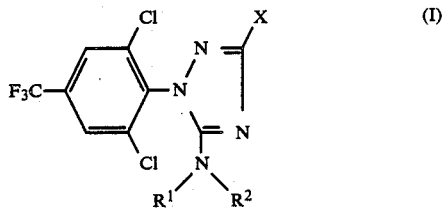

wherein X is a lower alkyl group having all or a part of hydrogen atoms substituted by fluorine atoms, and each of $R^1$ and $R^2$ which may be the same or different, is a hydrogen atom or a lower alkyl group, or $R^1$ and $R^2$ form together with the adjacent nitrogen atom a pyrrole ring or an ethoxymethylideneamino group.

21 Claims, No Drawings

PHENYLTRIAZOLE DERIVATIVE AND INSECTICIDE

This is a continuation-in-part of U.S. patent application Ser. No. 07/171,777 filed on Mar. 22, 1988, now U.S. Pat. No. 4,925,864.

BACKGROUND OF THE INVENTION

1. Field of the Invention

The present invention relates to a 1-phenyltriazole compound and an insecticide containing it as an active ingredient.

2. Discussion of Background

U.S. Pat. Nos. 4,038,405 and 4,097,599 disclose that triazole derivatives having a phenyl group at the 1-position and a trifluoromethyl group at the 3-position can be used as active ingredients of insecticides or miticides. Further, Belgian Patent Nos. 824,737 and 828,162 disclose that triazole compounds having a phenyl group at the 1-position and an organic phosphate residue at the 3-position are effective as insecticides, miticides and nematocides. Furthermore, European Patent Application No. EP 208321-A discloses that triazole derivatives having a substituted or unsubstituted phenyl group at the 1-position and a substituted or unsubstituted phenyl group at the 3-position are effective as insecticides or miticides.

However, the insecticidal activities of these compounds are not necessarily adequate.

SUMMARY OF THE INVENTION

The present inventors have synthesized various 1-phenyltriazole derivatives and conducted extensive studies on their physiological activities with an aim to develop a useful insecticide. As a result, it has been found that the compounds of the present invention have excellent insecticidal activities against various noxious insects, particularly against brown rice planthopper (*Nilaparvata lugens* Stal), small brown planthopper (*Laodelphax striatellus* Fallen) and rice water weevil (*Lissorhoptrus oryzophilus* Kuschel). The present invention is based on this discovery.

The present invention provides a phenyltriazole compound of the formula:

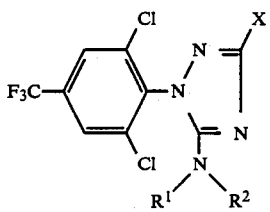

(I)

wherein X is a lower i.e. $C_1$–$C_6$ alkyl group having all or a part of hydrogen atoms substituted by fluorine atoms, and each of $R^1$ and $R^2$ which may be the same or different, is a hydrogen atom or a lower i.e. $C_1$–$C_6$ alkyl group, or $R^1$ and $R^2$ form together with the adjacent nitrogen atom a pyrrole ring or an ethoxymethylideneamino group.

DETAILED DESCRIPTION OF THE INVENTION

Now, the present invention will be described in detail with reference to the preferred embodiments.

In the phenyltriazole compound of the formula I, X is preferably a $C_1$–$C_3$ alkyl group having all or a part of hydrogen atoms substituted by fluorine atoms, such as $CF_3$, $C_2F_5$, $C_3F_7$ or $CH(CF_3)CH_3$.

Each of $R^1$ and $R^2$ which may be the same or different is preferably a hydrogen atom or a $C_1$–$C_4$ alkyl group. In a preferred embodiment, one of $R^1$ and $R^2$ is a hydrogen atom and the other is a $C_1$–$C_4$ alkyl group. In another preferred embodiment, $R^1$ and $R^2$ form together with the adjacent nitrogen atom a pyrrole ring or an ethoxymethylideneamino group.

Specific examples of the compound of the present invention will be presented in Table 1. Compound Nos. identified in the Table will be referred to in the following description.

TABLE 1

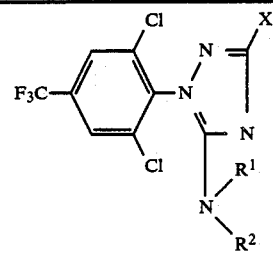

| Compound No. | X | $R^1$ / $R^2$ | Melting point (°C.) or refractive index$_D^{20}$ |
|---|---|---|---|
| 1 | $CF_3$ | $NH_2$ | 147–153 |
| 2 | $CF_3$ | $NHCH_3$ | 180–183 |
| 3 | $CF_3$ | $NHC_2H_5$ | 141–144 |
| 4 | $CF_3$ | $N(C_2H_5)_2$ | 58–60.5 |
| 5 | $C_2F_5$ | $NHCH_3$ | 159–162 |
| 6 | $C_2F_5$ | $NHC_2H_5$ | 124.5–127 |
| 7 | $C_2F_5$ | $NHC_3H_7$ | 96.5–98 |
| 8 | $C_3F_7$ | $NH_2$ | 168–171.5 |
| 9 | $C_3F_7$ | $NHC_2H_5$ | 108–110 |
| 10 | $CH(CF_3)CH_3$ | $NHCH_3$ | 169–171 |
| 11 | $CH(CF_3)CH_3$ | $NHC_2H_5$ | 82–83 |
| 12 | $CH(CF_3)CH_3$ | $NHC_3H_7$ | 73–74.5 |
| 13 | $CH(CF_3)CH_3$ | $NHC_3H_7$-iso | 1.4792 |
| 14 | $CH(CF_3)CH_3$ | $NHC_4H_9$ | 1.4838 |
| 15 | $CH(CF_3)CH_3$ | $N(C_3H_7)_2$ | 63–66 |
| 16 | $CH(CF_3)CH_3$ | $N=CHOC_2H_5$ | 1.4873 |
| 17 | $CH(CF_3)CH_3$ | 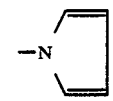 | 73.5–75 |

Particularly preferred specific compounds are as follows:

1-(2,6-dichloro-4-trifluoromethylphenyl)-5-(N-methylamino)-3-pentafluoroethyl-1H-1,2,4-triazole, 1-(2,6-dichloro-4-trifluoromethylphenyl)-5-(N-ethylamino)-3-pentafluoroethyl-1H-1,2,4-triazole, 1-(2,6-dichloro-4-trifluoromethylphenyl)-5-(N-propylamino)-3-pentafluoroethyl-1H-1,2,4-triazole, 1-(2,6-dichloro-4-trifluoromethylphenyl)-5-amino-3-heptafluoropropyl-1H-1,2,4-triazole, 1-(2,6-dichloro-4-trifluoromethylphenyl)-5-(N-methylamino)-3-(1-trifluoromethylethyl)-1H-1,2,4-triazole, 1-(2,6-dichloro-4-trifluoromethylphenyl)-5-(N-ethylamino)-3-(1-trifluoromethylethyl)-1H-1,2,4-triazole and 1-(2,6-dichloro-4-trifluoromethylphenyl)-5-(N-propylamino)-3-(1-trifluoromethylethyl)-1H-1,2,4-triazole.

The compounds of the present invention can be prepared in accordance with the following Reaction schemes.

REACTION SCHEME 1

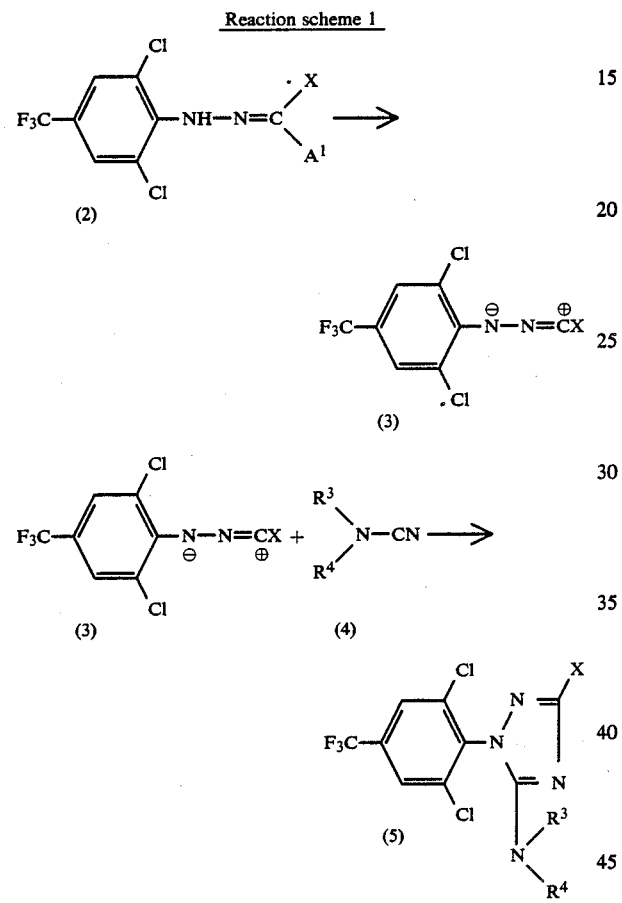

In the above formulas, $A^1$ is a halogen atom, each of $R^3$ and $R^4$ which may be the same or different is a hydrogen atom or a lower alkyl group, and X is as defined above.

In this reaction, a hydrazidoyl halide of the formula (2) is reacted with a base to form a nitrile imine intermediate of the formula (3).

The formed nitrile imine intermediate may be subjected, without being isolated, to the 1,3-cyclo addition reaction with a nitrile of the formula (4), whereby the desired compound of the formula (5) can be produced.

The base to be used here includes tertiary amines such as trialkylamines, N,N-dialkylanilines and aromatic amines. Such a base is used in an amount of from 1 to 3 molar times.

This reaction may be conducted in a suitable inert solvent or without using any solvent. The solvent may be an aromatic hydrocarbon compound such as benzene, toluene or xylene, a halogenated aromatic hydrocarbon compound such as chlorobenzene or dichlorobenzene, a halogenated aliphatic hydrocarbon compound such as carbon tetrachloride, chloroform or dichloromethane, or an ether such as diethyl ether or tetrahydrofuran. In a case where the nitrile of the formula (4) is liquid, an excess amount of the nitrile may be used as the solvent.

The reaction temperature and the reaction time vary depending upon the reactivity of the starting materials and can not generally be defined. However, in a case where the hydrazidoyl halide of the formula (2) is hydrazidoyl bromide, the reaction adequately proceeds at a temperature of from 10° to 80° C. for from 0.5 to 1 hour. Likewise, in the case of hydrazidoyl chloride, the desired compound can be produced in good yield by conducting the reaction within a temperature range of from 10° C. to the boiling point of the solvent used, preferably from 20° to 100° C. for from 1 to 10 hours.

By further alkylating the compound of the formula (5) of the present invention wherein $R^3$ and $R^4$ are hydrogen atoms, a different compound of the present invention can be obtained.

REACTION SCHEME 2

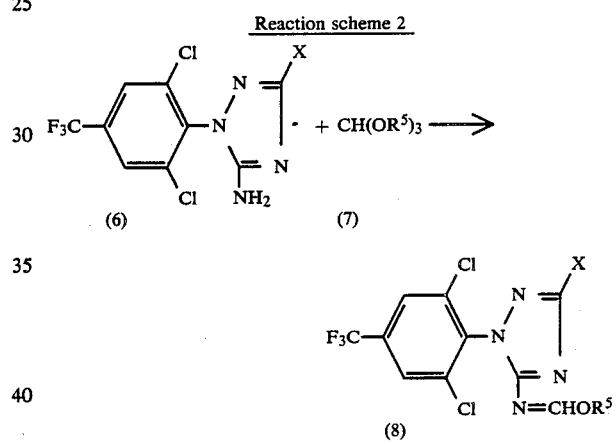

In the above formulas, $R^5$ is a lower alkyl group, and X is as defined above.

The alkoxymethylideneamino compound of the formula (8) can be prepared by reacting a 5-amino derivative of the formula (6) prepared by the Reaction scheme 1 with an alkyl orthoformate of the formula (7).

REACTION SCHEME 3

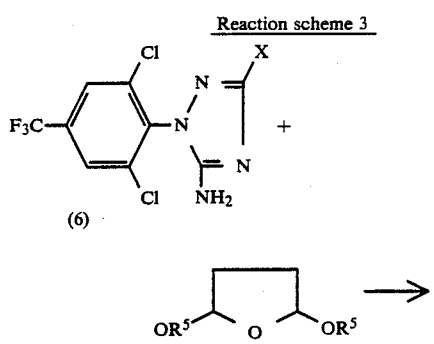

-continued
Reaction scheme 3

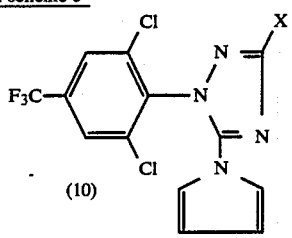

(10)

In the above formulas, X and $R^5$ are as defined above.

The 5-pyrrolyl compound of the formula (10) can be prepared by reacting a 5-amino derivative of the formula (6) prepared in accordance with the Reaction scheme 1, with a tetrahydrofuran derivative of the formula (9). The reaction may be conducted in an inert solvent at a temperature of from room temperature to 120° C. for from 0.5 to 1 hour whereby the desired product can be prepared in good yield.

Now, the processes for the production of the compounds of the present invention will be described with reference to Examples. However, it should be understood that the present invention is by no means restricted by such specific Examples.

EXAMPLE 1

Preparation of
1-(2,6-dichloro-4-trifluoromethylphenyl)-5-(N-ethylamino)-3-(1-trifluoromethylethyl)-1H-1,2,4-triazole (Compound No. 11)

7.8 g (0.02 mol) of 2-trifluoromethylpropionyl chloride 2,6-dichloro-4-trifluoromethylphenylhydrazone and 1.5 g (0.022 mol) of ethyl cyanamide were dissolved in 50 ml of tetrahydrofuran, and 2.5 g (0.025 mol) of triethylamine was dropwise added thereto under stirring and cooling with ice. After completion of the dropwise addition, the stirring was continued at room temperature for 3 hours. The solvent was distilled off under reduced pressure. The residue was dissolved in hexane, and the organic layer was washed with water and dried over anhydrous magnesium sulfate. Then, hexane was distilled off under reduced pressure. Further, the residue was subjected to distillation under reduced pressure. The fraction having a boiling point of 110°–120° C./0.1–0.2 mmHg was subjected to recrystallization from hexane to obtain 5.8 g (yield: 69%) of the desired compound having a melting point of from 82° to 83° C. as slightly yellow prismatic crystals.

EXAMPLE 2

Preparation of
1-(2,6-dichloro-4-trifluoromethylphenyl)-5-(N-propylamino)-3-(1-trifluoromethylethyl)-1H-1,2,4-triazole (Compound No. 12)

7.8 g (0.02 mol) of 2-trifluoromethylpropionyl chloride 2,6-dichloro-4-trifluoromethylphenylhydrazone and 1.9 g (0.002 mol) of propyl cyanamide were dissolved in 50 ml of tetrahydrofuran, and 2.6 g (0.026 mol) of triethylamine was dropwise added thereto under stirring and cooling with ice. After completion of the dropwise addition, the stirring was continued at room temperature for 2 hours. The solvent was distilled off under reduced pressure. The residue was dissolved in hexane, and the organic layer was washed with water and dried over anhydrous magnesium sulfate. Then, hexane was distilled off under reduced pressure. Further, the residue was subjected to distillation under reduced pressure. The fraction having a boiling point of 110°–120° C./0.1–0.2 mmHg was subjected to recrystallization from hexane to obtain 6.1 g (yield: 70%) of the desired compound having a melting point of from 73° to 74.5° C. as white prismatic crystals.

EXAMPLE 3

Preparation of
5-ethoxymethylideneamino-1-(2,6-dichloro-4-trifluoromethylphenyl)-3-(1-trifluoromethylethyl)-1H-1,2,4-triazole (Compound No. 16)

2.0 g (0.005 mol) of 5-amino-1-(2,6-dichloro-4-trifluoromethylphenyl)-3-(1-trifluoromethylethyl)-1H-1,2,4-triazole was added to 10 ml of ethyl orthoformate, and the mixture was refluxed under stirring for 2 hours. Then, excess ethyl orthoformate and ethanol thereby formed were distilled off under reduced pressure. The residue was purified by column chromatography to obtain 1.7 g (yield: 77%) of the desired compound as slightly yellow liquid. Refractive index $n_D^{20}$: 1.4873

EXAMPLE 4

Preparation of
1-(2,6-dichloro-4-trifluoromethylphenyl)-5-(1-pyrrolyl)-3-(1-trifluoromethylethyl)-1H-1,2,4-triazole (Compound No. 17)

3.9 g (0.01 mol) of 5-amino-1-(2,6-dichloro-4-trifluoromethylphenyl)-3-(1-trifluoromethylethyl)-1H-1,2,4-triazole and 1.3 g (0.01 mol) of 2,5-dimethoxytetrahydrofuran were dissolved in 15 ml of acetic acid, and the solution was refluxed under stirring for one hour. After cooling, the reaction solution was poured into water and neutralized with sodium hydrogencarbonate. Then, precipitates were extracted with ethyl acetate. The organic layer was washed with water and dried over anhydrous magnesium sulfate. The solvent was distilled off under reduced pressure, and the residue was purified by column chromatography to obtain 3 g (yield: 68%) of the desired compound having a melting point of from 73.5° to 75° C. as white powder.

The insecticide of the present invention comprises an insecticidally effective amount of the above described phenyltriazole compound as an active ingredient and an agricultural carrier. The phenyltriazole compound of the present invention can be used by itself as an insecticide, or by formulating it into a usual insecticidal formulation such as an emulsifiable concentrate, wettable powder, a dust or a granule by combining it with various adjuvants such as diluents, solvents, and surfactants.

The diluents include clay, talc, bentonite, diatomaceous earth and silica powder. The solvents include xylene, toluene, methyl ethyl ketone, isopropyl alcohol and dimethylnaphthalene. Surfactants include metal salts of an alkylbenzene sulfonic acid, polyoxyethylenealkylphenyl ethers, sodium alkylsulfate, a sodium alkylnaphthalene sulfonate and sodium lignin sulfonate. Other adjuvants include carboxymethylcellulose, polyethylene glycol and gum arabic.

The proportion of the active ingredient is suitable selected as the case requires. In the case of a dust or a granule, the proportion of the active ingredient is usually from 0.1 to 20% by weight, and in the case of an emulsifiable concentrate or wettable powder, it is usually from 5 to 80% by weight.

The insecticide of the present invention is diluted to a suitable concentration for application, or directly applied.

The insecticide of the present invention may be used for foliage application, soil treatment, treatment on the nursery box, treatment on water surface, etc.

The dose of the insecticide of the present invention varies depending upon the type of the compound used, the insect to be killed, the degree of outbreak, the degree of damage, the environmental conditions, the type of formulation to be used, etc. In the case of a dust or a granule which is applied by itself, the dose of an active ingredient is suitably selected within a range of from 0.1 g to 5 kg, preferably from 1 g to 1 kg, per 10 ares. In the case of an emulsifiable concentrate or a wettable powder which is eventually used in the form of a liquid, the concentration may suitably be selected within a range of from 0.1 to 10,000 ppm, preferably from 10 to 3,000 ppm.

The insecticide of the present invention can be used in combination with other insecticides or fungicides.

Now, Formulation Examples of the insecticide of the present invention will be given. However, it should be understood that the types and the proportions of the compounds and the adjuvants are not restricted by these specific Examples, and may be varied within wide ranges. In the following Examples, "%" means "%" by weight.

FORMULATION EXAMPLE 1

Emulsifiable Concentrate

30% of Compound No. 4, 20% of cyclohexanone, 11% of polyoxyethylenealkylaryl ether, 4% of calcium alkylbenzenesulfonate and 35% of methylnaphthalene were uniformly dispersed to obtain an emulsifiable concentrate.

FORMULATION EXAMPLE 2

Wettable Powder

40% of Compound No. 11, 15% of diatomaceous earth, 15% of clay, 25% of silica powder, 2% of sodium dinaphthylmethane disulfonate and 3% of sodium lignin sulfonate were uniformly mixed and pulverized to obtain a wettable powder.

FORMULATION EXAMPLE 3

Dust

Two % of compound No. 5, 5% of diatomaceous earth and 93% of clay were uniformly mixed and pulverized to obtain a dust.

FORMULATION EXAMPLE 4

Granule

Five % of Compound No. 12, 2% of sodium lauryl alcohol sulfate, 5% of sodium lignin sulfonate, 2% of carboxymethylcellulose and 86% of clay were uniformly mixed and pulverized. 100 Parts by weight of this mixture was kneaded with 20 parts by weight of water, and granulated to a size of from 14 to 32 mesh by an extrusion-type granulator, followed by drying to obtain a granule formulation.

The insecticide of the present invention exhibits excellent insecticidal activities against planthoppers such as brown rice planthopper (*Nilaparvata lugens* Stal), whitebacked rice planthopper (*Sogatella furcifera* Horvath) and small brown planthopper (*Laodelphax striatellus* Fallen), Coleoptera such as rice water weevil (*Lissorhoptrus oryzophilus* Kuschel) and it has extremely high penetration insecticidal activities. Further, it is also effective for the control of Hemiptera such as leaf hoppers, aphids and stink bugs, Lepidoptera such as diamondback moth (*Plutella xylostella* Linne) and common cutworm (*Spodoptera litura* Fabricius), Diptera such as housefly (*Musca domestica* Linne) and mosquito (*Culex pipiens pallens* Coquillett), Coleoptera such as adzuki bean weevil (*Callosobruchus chinensis* Linne) and scarabaeid (*Mimela splendens* Gyllenhal), Orthoptera such as German cockroach (*Blattela germanica* Linne) and mites such as twospotted spider mite (*Tetranychus urticae* Koch) and citrus red mite (*Paronychus citri* McGregor).

Now, the insecticidal activities of the compounds of the present invention will be described with reference to Test Examples.

TEST EXAMPLE 1

Insecticidal Activities Against Brown Rice Planthopper

The wettable powder prepared in accordance with Formulation Example 2 was diluted with water to a predetermined concentration. To this insecticidal solution, rice stem and leaf were dipped, and then dried in air and put in a test tube. Ten larvae of brown rice planthopper were put in the test tube, and the test tube was closed with a stopper of absorbent cotton. Then, the test tube was kept in a constant temperature chamber at 25° C. Six days later, the mortality was examined, and the mortality rate was calculated. The test was conducted in two series. The results are shown in Table 2.

TABLE 2

| | Mortality rate (%) Concentration of active ingredient (ppm) | |
|---|---|---|
| Compound No. | 100 | 20 |
| 1 | 100 | 100 |
| 2 | 100 | 100 |
| 3 | 100 | 100 |
| 4 | 100 | 100 |
| 5 | 100 | 100 |
| 6 | 100 | 100 |
| 7 | 100 | 100 |
| 8 | 100 | 100 |
| 9 | 100 | 100 |
| 10 | 100 | 100 |
| 11 | 100 | 100 |
| 12 | 100 | 100 |
| 13 | 100 | 100 |
| 14 | 100 | 100 |
| 15 | 100 | 100 |
| 16 | 100 | 100 |
| 17 | 100 | 100 |

TEST EXAMPLE 2

Insecticidal Activities Against Rice Water Weevil

The wettable powder prepared in accordance with Formulation Example 2 was diluted with water to bring the concentration of the active ingredient to a level of 100 ppm. This insecticidal solution was put in a polyethylene cup having a diameter of 9 cm, and ten adults of rice water weevil were put into the cup, and a cover was placed on the cup. Then, the cup was kept in a constant temperature chamber at 25° C. Two days later, the mortality was examined, and the mortality rate was calculated. The test was conducted in two series. The results are shown in Table 3.

TABLE 3

| Compound No. | Mortality rate (%) |
|---|---|
| 1 | 100 |
| 2 | 100 |
| 3 | 100 |
| 4 | 100 |
| 5 | 100 |
| 6 | 100 |
| 7 | 100 |
| 8 | 100 |
| 9 | 100 |
| 10 | 100 |
| 11 | 100 |
| 12 | 100 |
| 13 | 100 |
| 14 | 100 |
| 15 | 100 |
| 16 | 100 |
| 17 | 100 |
| Comparative compound 1 | 0 |
| Comparative Compound 2 | 0 |

The Comparative Compounds are as follows:
Comparative Compound 1:
1-phenyl-3-trifluoromethyl-1H-1,2,4-triazole (which is disclosed in U.S. Pat. No. 4,038,405)
Comparative Compound 2:
5-chloro-1,3-bis(2-chlorophenyl)-1H-1,2,4-triazole (which is disclosed in EP208321-A)
The same Comparative Compounds as above are used in the following tests.

TEST EXAMPLE 3

Insecticidal Activities Against Diamondback Moth

The wettable powder prepared in the same manner as in Formulation Example 2 was diluted with water to bring the concentration of the active ingredient to a level of 500 ppm. In this insecticidal solution, a leaf of cabbage was immersed, and then it was dried in air and put in a polyethylene cup having a diameter of 5.5 cm. Then, ten larvae of diamondback moth in third instar were put in the cup, and a cover was placed on the cup. Then, the cup was kept in a constant temperature chamber at 25° C. Three days later, the mortality was examined, and the mortality rate was calculated. The test was conducted in two series. The results are show in Table 4.

TABLE 4

| Compound No. | Mortality rate (%) |
|---|---|
| 1 | 100 |
| 3 | 100 |
| 4 | 100 |
| 5 | 100 |
| 6 | 100 |
| 7 | 100 |
| 8 | 100 |
| 9 | 100 |
| 11 | 100 |
| 13 | 100 |
| 15 | 100 |
| 16 | 95 |
| 17 | 90 |

TEST EXAMPLE 4

Penetration Test Against Small Brown Planthopper

The wettable powder prepared in accordance with the Formulation Example 2 was diluted with water to bring the concentration of the active ingredient to a level of 10 ppm. This insecticidal solution is put in a bottle, and the root portion of a rice seedling was dipped therein and fixed with a rubber stopper. A wire gauze cage was put thereon. Ten female adults of small brown planthopper were put therein, and a wire gauze cover was put thereon. Then, the wire gauze cage was kept in a constant temperature chamber at 25° C. Two days later, the mortality was examined and the mortality rate was calculated. The test was conducted in two series. The results are shown in Table 5.

TABLE 5

| Compound No. | Mortality rate (%) |
|---|---|
| 1 | 100 |
| 2 | 100 |
| 8 | 100 |
| 10 | 100 |
| 11 | 100 |
| 12 | 100 |
| 13 | 100 |
| 16 | 100 |
| Comparative compound 1 | 0 |
| Comparative Compound 2 | 0 |

TEST EXAMPLE 5

Insecticidal Activities Against Small Brown Planthopper

The wettable powder prepared in accordance with Formulation Example 2 was diluted with water to bring the concentration of the active ingredient to a level of 20 ppm. In this insecticidal solution, the foliage of a rice seedling was dipped for 10 seconds, and the root portion of the rice seedling was dipped in a bottle containing water and fixed with a rubber stopper. After drying the rice seedling in air, a wire gauze cage was put thereon. Ten female adults of small brown planthopper was put therein, and a wire gauze cover was placed thereon. Then, the wire gauze cage was placed in a constant temperature chamber at 25° C. Two days later, the mortality was examined, and the mortality rate was calculated. The test was conducted in two series. The results are shown in Table 6.

TABLE 6

| Compound No. | Mortality rate (%) |
|---|---|
| 3 | 100 |
| 7 | 100 |
| 10 | 100 |
| 11 | 100 |
| 12 | 100 |
| 13 | 100 |
| 14 | 100 |
| 16 | 100 |

What is claimed is:
1. A phenyltriazole compound having the formula:

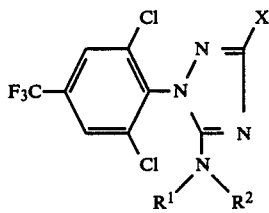

(I)

wherein X is a lower alkyl group having all or a part of hydrogen atoms substituted by fluorine atoms, and each of $R^1$ and $R^2$ which may be the same or different, is a hydrogen atom or a lower alkyl group, or $R^1$ and $R^2$ form together with the adjacent nitrogen atom a pyrrole ring or an ethoxymethylideneamino group.

2. The phenyltriazole compound according to claim 1, wherein X is a $C_1$–$C_3$ alkyl group having all or a part of hydrogen atoms substituted by fluorine atoms.

3. The phenyltriazole compound according to claim 1, wherein X is $CF_3$, $C_2F_5$, $C_3F_7$ or $CH(CF_3)CH_3$.

4. The phenyltriazole compound according to claim 1, wherein each of $R^1$ and $R^2$ which may be the same or different, is a hydrogen atom or a $C_1$–$C_4$ alkyl group.

5. The phenyltriazole compound according to claim 2, wherein each of $R^1$ and $R^2$ which may be the same or different, is a hydrogen atom or a $C_1$–$C_4$ alkyl group.

6. The phenyltriazole compound according to claim 3, wherein each of $R^1$ and $R^2$ which may be the same or different, is a hydrogen atom or a $C_1$–$C_4$ alkyl group.

7. The phenyltriazole compound according to claim 1, wherein one of $R^1$ and $R^2$ is a hydrogen atom and the other is a $C_1$–$C_4$ alkyl group.

8. The phenyltriazole compound according to claim 2, wherein one of $R^1$ and $R^2$ is a hydrogen atom and the other is a $C_1$–$C_4$ alkyl group.

9. The phenyltriazole compound according to claim 3, wherein one of $R^1$ and $R^2$ is a hydrogen atom and the other is a $C_1$–$C_4$ alkyl group.

10. The phenyltriazole compound according to claim 1, wherein $R^1$ and $R^2$ form together with the adjacent nitrogen atom a pyrrole ring or an ethoxymethylideneamino group.

11. The phenyltriazole compound according to claim 2, wherein $R^1$ and $R^2$ form together with the adjacent nitrogen atom a pyrrole ring or an ethoxymethylideneamino group.

12. The phenyltriazole compound according to claim 3, wherein $R^1$ and $R^2$ form tOgether with the adjacent nitrogen atom a pyrrole ring or an ethoxymethylideneamino group.

13. The phenyltriazole compound according to claim 1, which is 1-(2,6-dichloro-4-trifluoromethylphenyl)-5-(N-methylamino)-3-pentafluoroethyl-1H-1,2,4-triazole.

14. The phenyltriazole compound according to claim 1, which is 1-(2,6-dichloro-4-trifluoromethylphenyl)-5-(N-ethylamino)-3-pentafluoroethyl-1H-1,2,4-triazole.

15. The phenyltriazole compound according to claim 1, which is 1-(2,6-dichloro-4-trifluoromethylphenyl)-5-(N-propylamino)-3-pentafluoroethyl-1H-1,2,4-triazole.

16. The phenyltriazole compound according to claim 1, which is 1-(2,6-dichloro-4-trifluoromethylphenyl)-5-amino-3-heptafluoropropyl-1H-1,2,4-triazole.

17. The phenyltriazole compound according to claim 1, which is 1-(2,6-dichloro-4-trifluoromethylphenyl)-5-(N-methylamino)-3-(1-trifluoromethylethyl)-1H-1,2,4-triazole.

18. The phenyltriazole compound according to claim 1, which is 1-(2,6-dichloro-4-trifluoromethylphenyl)-5-(N-ethylamino)-3-(1-trifluoromethylethyl)-1H-1,2,4-triazole.

19. The phenyltriazole compound according to claim 1, which is 1-(2,6-dichloro-4-trifluoromethylphenyl)-5-(N-propylamino)-3-(1-trifluoromethylethyl)-1H-1,2,4-triazole.

20. An insecticide comprising an insecticidally effective amount of a phenyltriazole derivative of the formula I as defined in claim 1 and an agricultural carrier.

21. An insecticide comprising an insecticidally effective amount of a phenyltriazole derivative as defined in claim 18 and an agricultural carrier.

* * * * *